United States Patent [19]

Piorr et al.

[11] Patent Number: 4,990,288

[45] Date of Patent: * Feb. 5, 1991

[54] CONTROL OF DISALT IN α-SULFOFATTY ACID ESTER SURFACTANTS

[75] Inventors: Robert Piorr, Ratingen-Hoesel; Guenter Panthel, Haan; Karl H. Schmid, Mettmann; Dietmar Colignon, Erkrath; Hans J. Rommerskirchen, Duesseldorf-Eller; Wolfgang Schmidt, Monheim; Horst Ritterbex, Dusseldorf, all of Fed. Rep. of Germany

[73] Assignee: Henkel Kommanditgesellschaft auf Aktien, Duesseldorf-Holthausen, Fed. Rep. of Germany

[*] Notice: The portion of the term of this patent subsequent to Sep. 22, 2004 has been disclaimed.

[21] Appl. No.: 37,377

[22] Filed: Jun. 18, 1987

Related U.S. Application Data

[62] Division of Ser. No. 753,304, Jul. 10, 1985, Pat. No. 4,695,409.

[30] Foreign Application Priority Data

Sep. 3, 1984 [DE] Fed. Rep. of Germany ....... 3432324

[51] Int. Cl.$^5$ .................... C07B 45/02; C07C 309/62; C07C 309/22; C07C 309/17
[52] U.S. Cl. ...................................................... 260/400
[58] Field of Search ........................................ 260/400

[56] References Cited

U.S. PATENT DOCUMENTS 4,695,409 9/1987 Piorr et al. ........................... 260/400
4,820,451 4/1989 Piorr et al. ........................... 260/400

Primary Examiner—Carolyn S. Elmore
Attorney, Agent, or Firm—Ernest G. Szoke; Wayne C. Jaeschke; Henry E. Millson, Jr.

[57] ABSTRACT

In light colored surfactants produced by sulfonation of fatty acid alkyl esters with less than 2 moles of $SO_3$ per mole of fatty acid alkyl ester and subsequent work-up of the crude sulfonate in aqueous medium to form salts, the content of α-sulfofatty acid disalts is regulated and reduced by transesterifying the sulfonation product before its treatment with an aqueous medium with at least about 0.5 mole equivalent of an alcohol, based on the $SO_3$ which is not for α-sulfonation.

14 Claims, No Drawings

CONTROL OF DISALT IN α-SULFOFATTY ACID ESTER SURFACTANTS

This application is a division of application Ser. No. 753,304, filed July 10, 1985, now U.S. Pat. No. 4,695,409.

BACKGROUND OF THE INVENTION

1. Field of the Invention

The present invention relates to a method for regulating the disalt content in α-sulfofatty acid ester surfactants in the process for the manufacture thereof.

2. Description of Related Art

Wash-active substances based on α-sulfofatty acid esters or their salts have been known for decades and numerous processes have been proposed for their production (see e.g. U.S. Pat. No. 2,195,187, U.S. Pat. No. 3,256,303 and U.S. Pat. No. 3,158,632). The salts of α-sulfofatty acid esters acting as wash-active substances are obtained by sulfonation of lower alkyl esters of saturated higher fatty acids with sulfur trioxide. In particular, fatty acid methyl esters which contain from 6 to 28 carbon atoms in the fatty acid residue and which, apart from the $CH_2$-group in the α-position of the fatty acid residue, contain no other sulfonatable or sulfatable groups and which have an iodine number below 5, are sulfonated with a sulfur trioxide-inert gas mixture and the reaction product is neutralized. Since dark-colored crude products regularly accumulate during the sulfonation reaction, being unsuitable for use in detergents and cleaners in that form, the crude sulfonation product has to be bleached. $H_2O_2$ and/or hypochlorite in aqueous solution is/are normally used for bleaching.

It is also known that considerable quantities of disalt of the corresponding α-sulfofatty acids accumulate as an undesirable secondary product during this sulfonation of fatty acid esters and during work-up of the α-sulfofatty acid ester crude product with aqueous media. These disalts of the α-sulfofatty acids are undesirable for several reasons. First of all, they show only limited solubility in water. Secondly, they exhibit poor surface activities Above all, however, they deteriously influence the viscosity of the aqueous ester sulfonate pastes ultimately produced. An excessive content of the disalts accumulating as secondary product leads to a considerable increase in the viscosity of the aqueous ester sulfonate pastes which in turn gives rise to difficulties during further processing of the ester sulfonate surfactant.

Considerable attention has been devoted, especially in recent years, to this particular aspect of the production of surfactants based on ester sulfonates. Numerous difficulties result, cf. U.S. Pat. No. 4,404,143 and German Offenlegungsschrift No. 33 34 517. According to the first of these two publications a highly concentrated aqueous solution of a salt of α-sulfofatty acid esters is prepared by neutralizing the sulfonated fatty acid ester product with an aqueous alkali solution in two stages, in the first of which the sulfonated product is neutralized to a pH-value of from 2.5 to 4 with an aqueous alkali solution of relatively high concentration (15 to 50% by weight of alkali) in the presence of a $C_1$–$C_4$ alcohol in a quantity of from 5 to 20% by weight, based on the weight of the sulfonated product, after which neutralization is completed to a pH-value of from 6 to 7 in a second stage carried out with a less concentrated aqueous alkali solution. The crude sulfonation product may optionally be bleached before this two-stage neutralization. To this end, an aqueous solution of $H_2O_2$ is preferably used again in the presence of a $C_1$–$C_4$ alcohol. The hydrogen peroxide is supposed to be used in the form of an aqueous solution having a concentration of 10% by weight or higher. The preferred alcohol is methanol where the fatty acid esters are methyl esters. Utilizing this technique is said to reduce the disalt content of the corresponding α-sulfofatty acids to 5% or lower.

However, the second of the two above-mentioned publications, German Application No. 33 34 517, describes the disadvantages of this process. The sulfonation products obtained contain the short-chain alcohol used in a large excess in the aqueous neutralized reaction product. These comparatively large quantities of free alcohol are again undesirable for a number of reasons. They are troublesome, for example, during the work-up of surfactant mixtures of the above type in the production of detergent mixtures by spray-drying, particularly giving rise to undesirable pluming. In addition, the free alcohols present in the surfactant mixture have an unpleasant odor which necessitates deodorization. To solve these problems, German Offenlegungsschrift No. 33 34 517 proposes carrying out the aqueous bleaching and neutralization of the crude α-sulfofatty acid esters in the presence of such quantities of a lower alcohol that an aqueous suspension containing from 30 to 55% by weight of the α-sulfofatty acid ester salt and, based on the weight of the α-sulfofatty acid ester salt, from 5 to 15% by weight of a lower alcohol sulfate and from 8 to 40% by weight of the lower alcohol is obtained. Finally, the aqueous suspension is said to be concentrated in such a way that it contains from 40 to 65% by weight of α-sulfofatty acid ester salt, from 2 to 10% by weight of a lower alcohol sulfate and at most 2% by weight of a lower alcohol.

DESCRIPTION OF THE INVENTION

Other than in the operating examples, or where otherwise indicated, all numbers expressing quantities of ingredients or reaction conditions used herein are to be understood as modified in all instances by the term "about".

The present invention is based on the surprising observation that the undesirable formation of α-sulfofatty acid disalts can be prevented in a very much more practical manner. There is no need for large excesses of alcohol to be used or for the optional subsequent step or concentration by evaporation to eliminate unwanted alcohol. The process of the present invention is based on the realization that measured treatment of the crude sulfonate of fatty acid alkyl esters with any alcohol in a small, but defined quantity, as explained hereinafter, results in the controllable reduction of the content of unwanted disalt. It is also possible by this measure to produce interesting ester mixtures of α-sulfofatty acids which are distinguished, for example, by improved flow properties during further processing.

Accordingly, the present invention relates to a process for regulating and reducing the content of α-sulfofatty acid disalts in light-colored surfactants and surfactant mixtures which are produced by Sulfonation of fatty acid alkyl esters with more than 1 and less than 2 moles of $SO_3$ mole of fatty acid alkyl ester and subsequent work-up of the crude sulfonate in aqueous medium to form salts. In the process of the invention, before the treatment with an aqueous medium, the sulfonation product is transesterified with at least about 0.5 mole equivalent of an alcohol, based on the quantity of SO₃ which is not used for α-sulfonation.

In one particularly preferred embodiment of the process of the invention, the free alcohol content of the reaction product is limited at the same time. To this end, no more than about 2 mole equivalents of the free alcohol component are used in the transesterification stage. More particularly, no more than about 1 5 mole equivalents of the alcohol are used in the transesterification stage. These mole equivalents are again based on the quantity of SO₃ which is present in the crude sulfonation product i e. which has not been used for α-sulfonation This S₃ reference base is calculated as the sum of two partial amounts. One of these partial amounts corresponds to the SO₃ excess which has been used in the sulfonation step (to increase the conversion) over and above the quantity of SO₃ required for α-sulfonation. The other partial amount is the difference between the quantity of SO₃ theoretically required and the amount actually used in the α-sulfonation step.

The quantity of alcohol used for transesterification in each individual case may be determined in part from the composition of the alcohol. Thus, in one preferred embodiment of the invention, alcohols which show comparatively high reactivity in the transesterification step are used in smaller quantities (within the ranges indicated) than less reactive alcohols. As a general rule, quantities of no more than about 1.3 mole equivalents of the alcohol, based on the excess quantity of SO₃ described above, can be used with advantage; quantities of from 0.8 to 1.3 mole equivalents of alcohol being preferred and quantities of from 0.9 to 1.1 mole equivalents of alcohol being particularly preferred.

The conditions for the transesterification reaction are selected in such a way, with particular allowance for the reactivity of the alcohol used for transesterification, that the additional heat load on the reaction mixture is kept to a minimum. In this way, the formation of undesirable, additional discolorations in the reaction product can be limited or prevented. However, the reaction conditions have to be sufficiently intensive to bring about the transesterification required in accordance with the invention. As a general rule, esterification is carried out at temperatures of from 40° to 150° C. and preferably at temperatures not exceeding 120° C. Suitable temperatures are temperatures above 60° C. and, more particularly, above 70° C. A suitable temperature range is, for example, 75° to 100° C. The reaction time is determined by, and is dependent on, the reactivity of the alcohol used for transesterification, the reaction temperature selected, and the required reduction in the disalt content. In general, the reaction time is at least 5 minutes and, more particularly, at least 10 minutes. Normally, a reaction time of from 10 to 30 minutes is suitable.

The following general rule applies to the choice of the process conditions. Lower alcohols, particularly monohydric lower alcohols, for example containing from 1 to 5 carbon atoms, show comparatively high reactivity in the transesterification reaction, although lower polyhydric alcohols also show comparatively high reactivity. In general, higher monohydric or polyhydric alcohols show lower reactivity Fatty alcohols or wax alcohols are examples of less reactive alcohols. Accordingly, their use requires more intensive reaction conditions within the above-stated limits.

As a consequence of the transesterification reaction, the free alcohol used for the reaction is bound in ester form to the α-sulfofatty acid. The alcohol component originally present in the fatty acid ester used is split off as alcohol sulfate and, for example where fatty acid methyl esters are used as starting material for the sulfonation reaction, is present as methyl sulfate in the reaction mixture after transesterification The choice of the reaction components and reaction conditions within the parameters given above results in a disalt content in the reaction product treated with aqueous media and neutralized of less than 10% by weight, based on wash-active substance. Disalt contents of 5% or less by weight are preferred and can readily be obtained, although it is possible to obtain even lower disalt contents, for example less than 2% by weight, using the process of the invention. Where highly reactive alcohols are used in the transesterification stage, hardly any detectable alcohol is present in the ester sulfonate paste. Where less reactive alcohols are used, limited quantities of the free alcohol used in a small excess may be tolerated in the product to achieve acceptable reaction times in the reduction of the disalt content to below the indicated limits.

In principle, any alcohol can be used as the alcohol component for the transesterification step. Accordingly, suitable alcohols are both monohydric alcohols and polyhydric alcohols. In one important embodiment of the invention, the same alcohol which is present in the fatty acid alkyl ester starting material is used for transesterification. More particularly aliphatic $C_1$–$C_3$ monoalcohols and the corresponding fatty acid alkyl esters are used with methanol and the corresponding fatty acid methyl esters are preferred. Since these lower alcohols and especially methanol are distinguished by high reactivity in the transesterification step, the quantity of free alcohol used can readily be limited to the quantity which corresponds to the SO₃ that is not used for α-sulfonation. At the same time, comparatively milder conditions can be applied with respect to temperature and/or reaction time. The result of the transesterification step according to the invention is an α-sulfofatty acid alkyl ester, more particularly a methyl ester, in admixture with a small quantity of methyl sulfate which is substantially free from disalts and which does not contain any detectable quantities of free alcohol.

In one particularly important embodiment of the invention, however, the alcohols used for transesterification are different from those present in the fatty acid ester starting material. In this case, too, the alcohols used may be divided into two basic groups, namely: monohydric and/or polyhydric alcohols which, on reaction with free SO₃, are capable of forming capillary-active surfactant-like sulfates, and monohydric and/or polyhydric alcohols which, on reaction with free SO₃, form non-capillary-active sulfates.

The second of these two groups includes in particular alcohols containing a limited number of carbon atoms, for example monohydric alcohols containing no more than 9 carbon atoms. However, it also includes lower polyols, for example ethylene glycol or glycerol. The group of alcohols which, on reaction with free SO₃, are capable of forming capillary-active surfactant-like sulfates includes compounds which contain at least one hydrophobic residue and at least one aliphatically bound hydroxyl group on the molecule. The hydrophobic residue present in these hydroxyl compounds can be a hydrocarbon residue containing at least 10 carbon atoms, more particularly an aliphatic or cycloaliphatic hydrocarbon residue. The hydrophobic residue can contain, for example, up to 30 carbon atoms.

This second group of alcohols includes, for example, saturated fatty alcohols or fatty alcohol mixtures of natural or synthetic origin or fatty acid alkylol amides. Like the starting material for the sulfonation step, these hydroxyl compounds can also have been obtained from naturally occurring fats and oils. Instead of fatty alcohols or fatty acid alkylolamides such as these, it is possible to use any other hydroxyl compounds which are capable of forming capillary-active substances upon reaction with free $SO_3$. Hydroxyl compounds such as these include partial ethers of polyhydric alcohols with fatty alcohols and partial esters of polyhydric alcohols with fatty acids, for example partial ethers and partial esters of ethylene glycol, propylene glycol, glycerol, pentaerythritol, mannitol, hexitol and also partial ethers and partial esters of polyethylene and/or polypropylene glycols, polyglycerols, polypentaerythritol and the like. Suitable compounds are, above all, polyglycol ethers of the type obtained by the addition of ethylene and/or propylene oxide onto fatty alcohols, fatty acids, fatty acid amides or onto the partial ethers or partial esters of fatty alcohols and fatty acids containing dihydric, trihydric and polyhydric alcohols.

In one preferred embodiment, the alcohols used for transesterification, apart from the hydroxyl group, contain no reactive groups in the molecule which are capable of undesirable secondary reactions.

Suitable alcohol components are, for example, monohydric aliphatic and cycloaliphatic $C_1$–$C_{30}$ and preferably $C_1$–$C_{24}$ such as methanol, ethanol, n-propanol, i-propanol, n-butanol, 2-butanol, n-pentanol, 2-pentanol, n-hexanol, n-octanol, n-decanol, n-dodecanol, n-tetradecanol, n-hexadecanol, n-octadecanol, n-eicosanol, n-docosanol, 2-hexyldecanol, 2-octyldodecanol, 2-dodecylhexadecanol, $C_9$–$C_{18}$ oxoalcohols, $C_8$–$C_{20}$ Ziegler alcohols, cyclohexanol and methylcyclohexanols; $C_2$–$C_{30}$ polyhydric aliphatic and cycloaliphatic alcohols, such as ethylene glycol, 1,2-propylene glycol, 1,3-propylene glycol, 1,2-butylene glycol, 1,4-butylene glycol, hexamethylene glycol, polyethylene glycols, polypropylene glycols, glycerol, polyglycerols, trimethylol ethane, trimethylol propane, pentaerythritol, dipentaerythritol, mannitol, sorbitol, 1,2-cyclohexane diol and 1,3,5-cyclohexanetriol. The alcohols mentioned may be used individually or in admixture in the process of the invention. Commensurate with their origin, fatty alcohols in the narrower sense, i.e. straight-chain aliphatic $C_8$–$C_{24}$ alcohols, are generally used in the form of mixtures, the composition of these mixtures being determined by the natural fats and oils which are used as starting materials in their production.

Other examples of useful alcohol components are glycol semiethers, such as methyl ethylene glycol, ethyl ethylene glycol and adducts of from 1 to 20 moles of ethylene oxide and/or propylene oxide with aliphatic $C_1$–$C_{24}$ alcohols, particularly with fatty alcohols and fatty alcohol mixtures; glycol semi-esters, such as ethylene glycol monolaurate, ethylene glycol monomyristate and propylene glycol monostearate and adducts of from 1 to 20 moles of ethylene and/or propylene oxide with aliphatic $C_1$–$C_{24}$ carboxylic acids, more especially with fatty acids and fatty acid mixtures; glycerol partial ethers and partial esters, such as glycerol monodecyl ether, glycerol monoacetate, glycerol diacetate, glycerol monopalmitate, glycerol distearate and ethylene oxide and/or propylene oxide adducts of these glycerol derivatives; fatty acid alkanolamides, such as lauric acid monoethanolamide, lauric acid diethanolaaide, stearic acid diethanolamide, and ethylene oxide and/or propylene oxide adducts with carboxylic acid amides, particularly with fatty acid amides.

In the preferred embodiment of the process of the invention, the crude sulfonate to be subjected to transesterification should contain no more than 50 mole % and preferably no more than 25 mole %, based on the α-sulfofatty acid ester formed of $SO_3$ which is not used in the α-sulfonation step. In addition, the degree of sulfonation of the fatty acid ester used as starting material in the crude sulfonates should preferably be at least 90%, more preferably at least 95% and, better still, 98% or higher.

The sulfonation step preceding the transesterification step is carried out in accordance with the teachings of the prior art, see for example U.S. Pat. No. 3,256,303 and U.S. Pat. No. 3,158,632. The starting material for this sulfonation step is preferably a lower alkyl ester, more particularly the methyl ester, of fatty acids containing for example from 6 to 28 and preferably from 8 to 18 carbon atoms. These fatty acid residues preferably emanate from natural fats of vegetables, land animals or aquatic animals. Apart from the hydrogen atom in the α-position, they should not contain any other sulfatable or sulfonatable groups, particularly double bonds or alcoholic hydroxyl groups. Their iodine numbers are below 5 and preferably below 2. Sulfonation is carried out with an $SO_3$-inert gas mixture which, normally, may contain from 2 to 40% by volume of $SO_3$ at temperatures not exceeding or not significantly exceeding 100° C. and, preferably, not exceeding 95° C. The process can be carried out at a constant temperature or at a temperature adjusted in stages, as described in the above-mentioned publications.

The transesterification step of the invention is followed by working up the reaction product with aqueous media in known manner. This work-up step comprises, in particular, the bleaching and neutralization of the crude sulfonate transesterified in accordance with the invention. Bleaching can be carried out in known manner with aqueous hydrogen peroxide and/or hypochlorite solution. Neutralization can be carried out either before or after bleaching. Acidic bleaching with hydrogen peroxide is described, for example, in U.S. Pat. No. 3,159,657, while U.S. Pat. No. 3,452,064 describes a combined bleaching treatment in which an initially acidic peroxide bleaching operation is followed by neutralization of the sulfonated and partially bleached material, after which bleaching is completed with hydrogen peroxide or, better still, with hypochlorite.

The process conditions used for bleaching and/or neutralization have to be selected in such a way that the theoretically possible hydrolysis of the esters is precluded or suppressed as far as possible. In the absence of these precautionary measures, the advantages of the transesterification step of the invention with respect to reduction of the disalt content would be at least partly forfeited.

By reacting the crude sulfonic acid products with the alcohols in accordance with the invention to produce the required transesterification, it is possible not only to reduce the disalt content, but also to establish a broad spectrum of new ester sulfonate mixtures (for example methyl ester sulfonate+ester sulfonate of the alcohol used for transesterification) showing different performance properties. The invention thus opens up an interesting way of producing aqueous suspensions or pastes of ester sulfonates having a high content of α-sulfofatty acid ester salts and, at the same time, a low viscosity. This low viscosity is achieved on the one hand through the reduction in the undesired disalt content of the ester sulfonate paste, and on the other hand sulfonate ester mixtures can also lead to a reduction in viscosity in pastes of high fatty content (cf. German application No. 33 34 517 cited above).

A general procedure for carrying out the transesterification reaction according to the invention is described in the following Examples which are not given for purposes of limitation. The following Table shows the particular alcohol components used for transesterification, the reaction times and reaction temperatures used, the molar ratio of the SO₃ not used for α-sulfonation in the crude sulfonate to the quantity of the alcohol used for transesterification and the values finally obtained for the disalt content in % by weight, based on the wash-active substance.

EXAMPLES

Examples 1 to 16

283 g (1 mole) of hardened tallow fatty acid methyl ester (iodine number 0.5; saponification number 198) were sulfonated with 96 g (1.2 moles) of sulfur trioxide (5% by volume in air) at 90° C. in a falling-film reactor. The resulting reaction mixture was then tempered for 30 minutes at 90° C. Thereafter the degree of sulfonation was 98%.

7.0 g (0.22 mole) of methanol were added to the tempered, crude sulfonation product with stirring at 90° C., followed by stirring for 20 minutes at 90° C. 16 g of hydrogen peroxide in the form of a 35% by weight aqueous solution were added to the reaction product for bleaching, after which the product was stirred for 10 minutes at 60° C. before it was neutralized to pH 7 by the addition of a 25% by weight sodium hydroxide solution. In the solution of the neutral salt obtained in this way, the disalt content amounted to 5.2% by weight, based on the total quantity of wash-active substance.

The disalt content was determined by potentiometric titration of an aqueous solution, adjusted to pH 2.5-3, of the bleached and neutralized sulfonation product with sodium hydroxide solution, taking into account the fatty acid fractions present in the unsulfonated material.

In Examples 2 to 17, the procedure described above was modified to the extent that transesterification was carried out with the alcohols indicated in the following Table instead of methanol. In Example 17, a comparison test was carried out under the same conditions as in Example 1, but without transesterification between sulfonation and bleaching.

The results obtained in Examples 1 to b 16 are shown in the following Table.

TABLE

Transesterification of crude sulfonation products of hardened tallow fatty acid methyl ester at 90° C.

| Example No. | Alcohol component | Reaction time (mins.) | SO₃ excess: alcohol (mole/mole equiv.) | Disalt content (% by wt) |
|---|---|---|---|---|
| 1 | methanol | 20 | 1:1 | 5.2 |
| 2 | ethanol | 20 | 1:1 | 6.8 |
| 3 | n-propanol | 20 | 1:1 | 6.6 |
| 4 | n-butanol | 20 | 1:1 | 7.6 |
| 5 | n-octanol | 20 | 1:1 | 6.0 |
| 6 | 2-ethylhexanol | 20 | 1:1 | 6.4 |
| 7 | lauryl/myristyl-alcohol (molar ratio 3:1) | 20 | 1:1 | 5.5 |
| 8 | ethylene glycol | 10 | 1:1 | 8.2 |
| 9 | ethylene glycol | 20 | 1:1 | 6.1 |
| 10 | glycerol | 10 | 1:1 | 9.1 |
| 11 | glycerol | 20 | 1:1 | 6.6 |
| 12 | oleyl alcohol + 1 PO + 6 EO | 10 | 1:1 | 12.0 |
| 13 | oleyl alcohol + 1 PO + 6 EO | 20 | 1:1 | 7.6 |
| 14 | 2-ethoxy ethanol | 20 | 1:1 | 7.1 |
| 15 | 2-ethoxy ethanol | 20 | 1:0.7 | 5.3 |
| 16 | methanol | 20 | 1:3 | 1.6 |
| 17 | none (comparison test) | — | — | 22.7 |

What is claimed is:

1. A process for the preparation of α-sulfofatty acid alkyl esters having a low disalt content comprising the steps of:
   A. sulfonating a fatty acid alkyl ester with more than 1 but less than 2 moles of SO₃ per mole of fatty acid alkyl ester to produce an α-sulfofatty acid alkyl ester;
   B. at least partially transesterifying the α-sulfofatty acid alkyl ester from step A with an at least about 0.5 mole equivalent, based on the quantity of SO₃ which is not used for a α-sulfonation of an alcohol different from the alcohol forming the ester moiety of the α-sulfofatty acid alkyl ester, at a temperature of from about 40° to about 150° C., to form a reaction mixture containing transesterified α-sulfofatty acid alkyl ester and alkyl sulfate; and
   C. working up the product mixture from step B in an aqueous medium to form salts of α-sulfofatty acid alkyl esters present in the mixture.

2. A process in accordance with claim 1, wherein from about 0.9 to about 1.1 mole equivalents of the alcohol are used for transesterification in step B.

3. A process in accordance with claim 1, wherein the temperature in step B is from about 70 to about 120° C.

4. A process in accordance with claim 1, wherein the temperature in step B is from about 75 to about 100° C.

5. A process in accordance with claim 1 wherein the alcohol moiety in the fatty acid alkyl ester starting material in step A is derived from one or more aliphatic C₁-C₃ monoalcohols.

6. A process in accordance with claim 5 wherein the fatty acid alkyl ester starting material is a methyl ester.

7. A process in accordance with claim 1, wherein the alcohol in step B is a monohydric alcohol, a polyhydric alcohol, or a mixture of the foregoing which form capillary-active surfactant-like sulfates upon reaction with free SO₃.

8. A process in accordance with claim 1, wherein the alcohol in step B is a monohydric alcohol, a polyhydric alcohol, or a mixture of the foregoing which form non-capillary-active sulfates upon reaction with free SO₃.

9. A process in accordance with claim 1 wherein in step A the resulting reaction mixture contains no more than 50 mole % free $SO_3$ based on a α-sulfofatty acid ester.

10. A process in accordance with claim 9 wherein no more than about 25 mole % of free $SO_3$ is present.

11. A process in accordance with claim 1 wherein the degree of sulfonation of the fatty acid alkyl ester starting material in step A is at least 90%.

12. A process in accordance with claim 11 wherein the degree of sulfonation is at least 95%.

13. The process of claim 1, wherein the alcohol in step B is a $C_1$–$C_5$ monohydric or polyhydric alcohol.

14. The process of claim 1 wherein in step B the reaction mixture also contains non-transesterified α-sulfofatty acid alkyl ester.

* * * * *